(12) United States Patent
Peters et al.

(10) Patent No.: US 12,027,241 B2
(45) Date of Patent: Jul. 2, 2024

(54) METHODS AND SYSTEMS FOR IN-CLINIC COMPLIANCE PROTOCOLS

(71) Applicant: IDEXX Laboratories, Inc., Westbrook, ME (US)

(72) Inventors: Elizabeth Peters, Freeport, ME (US); Jeffrey Lott, Plano, TX (US); Matt Spradley, Frisco, TX (US); Matt Russell, Frisco, TX (US); Tanya Jarosz, Wells, ME (US)

(73) Assignee: IDEXX Laboratories, Inc., Westbrook, ME (US)

( * ) Notice: Subject to any disclaimer, the term of this patent is extended or adjusted under 35 U.S.C. 154(b) by 797 days.

(21) Appl. No.: 17/095,849

(22) Filed: Nov. 12, 2020

(65) Prior Publication Data

US 2021/0151134 A1 May 20, 2021

Related U.S. Application Data

(60) Provisional application No. 62/935,844, filed on Nov. 15, 2019.

(51) Int. Cl.
*G16H 20/00* (2018.01)
*G16H 10/00* (2018.01)
*G16H 50/30* (2018.01)

(52) U.S. Cl.
CPC ............ *G16H 10/00* (2018.01); *G16H 20/00* (2018.01); *G16H 50/30* (2018.01)

(58) Field of Classification Search
CPC ........ G16H 10/00; G16H 20/00; G16H 50/30; G16H 10/60; G16H 15/00; G16H 20/10;
(Continued)

(56) References Cited

U.S. PATENT DOCUMENTS

2006/0106645 A1* 5/2006 Bergelson ............... G16H 40/20
705/3
2007/0061170 A1* 3/2007 Lorsch .................... G16H 30/20
705/3

(Continued)

FOREIGN PATENT DOCUMENTS

CA          3126386 A1 *  7/2019   ........... A01K 11/006

OTHER PUBLICATIONS

International Search Report and Written Opinion prepared by the European Patent Office in International Application No. PCT/US2020/060088, dated Feb. 16, 2021.

*Primary Examiner* — John A Pauls
(74) *Attorney, Agent, or Firm* — McDonnell Boehnen Hulbert & Berghoff LLP

(57) ABSTRACT

An example computer-implemented method of increasing veterinary health care compliance includes receiving information indicating that an animal patient concluded a visit at a veterinary practice, in response accessing diagnostic test results for the animal patient, based on the diagnostic test results creating a pet owner profile for an owner of the animal patient, matching the pet owner profile with a stored message and stored information relating to a product associated with recommended treatment for the animal patient, sending an electronic message to a second computing device associated with the owner of the animal patient that includes the stored message and the stored information relating to the product associated with recommended treatment for the animal patient, receiving a report indicating whether the owner of the animal patient obtained the product associated with recommended treatment for the animal patient, and updating the pet owner profile to be indicative of the report.

15 Claims, 3 Drawing Sheets

(58) Field of Classification Search
CPC ........ G16H 20/30; G16H 20/40; G16H 20/60; G16H 70/20; G16H 40/67
See application file for complete search history.

(56) References Cited

U.S. PATENT DOCUMENTS

| | | | |
|---|---|---|---|
| 2008/0103371 A1* | 5/2008 | Rosenblum | G16H 20/30 600/300 |
| 2009/0138285 A1* | 5/2009 | Denberg | G16H 10/60 707/E17.014 |
| 2012/0124387 A1* | 5/2012 | Skocic | A01K 11/006 713/186 |
| 2014/0156311 A1* | 6/2014 | Shenoy | G16H 10/40 705/3 |
| 2015/0112722 A1* | 4/2015 | Dees | A61B 5/7275 705/3 |
| 2015/0294072 A1 | 10/2015 | Lyle et al. | |
| 2016/0012748 A1 | 1/2016 | Donavon | |
| 2016/0063188 A1 | 3/2016 | Thornberry et al. | |
| 2019/0095822 A1* | 3/2019 | Rugel | G06N 20/00 |
| 2019/0214116 A1* | 7/2019 | Eberting | G16H 40/20 |

* cited by examiner

METHODS AND SYSTEMS FOR IN-CLINIC COMPLIANCE PROTOCOLS

CROSS REFERENCE TO RELATED APPLICATION

The present disclosure claims priority to U.S. provisional application No. 62/935,844, filed on Nov. 15, 2019, the entire contents of which are herein incorporated by reference.

FIELD

The present disclosure relates generally to methods for generating and sending prescribed protocols electronically with information specific for recommended treatment and products based on diagnostic results of an animal patient following a visit to a veterinary practice.

BACKGROUND

Many pet owners are diligent with respect to scheduling regular check-ups at a veterinary practice. Based on results of the visit, certain treatment plans are often recommended. Whether the pet owner follows the treatment plan can be difficult to verify, however. It would be desirable to provide pet owners with timely information for successful at-home care, and possible products to assist with treatment, and to know if they purchased and what they purchased, based upon a prescribed protocol.

SUMMARY

Implementations disclosed herein relate to computer-implemented methods of increasing veterinary health care compliance. Example methods include creating a pet owner profile for an owner of the animal patient based on diagnostic test results for the animal patient, and matching, within a product database, the pet owner profile with a stored message and stored information relating to a product associated with recommended treatment for the animal patient.

Some implementations disclosed herein are additionally or alternatively directed to generating and sending an electronic message to a second computing device associated with the owner of the animal patient that includes personalized message(s) and customized protocols linking products available for delivery of products associated with recommended treatment for the animal patient.

Some implementations disclosed herein are additionally or alternatively directed to particular technique(s) for receiving a report indicating whether the owner of the animal patient obtained the product associated with recommended treatment for the animal patient, and updating, in the veterinary patient information database, the pet owner profile to be indicative of the report.

The above description is provided as an overview of some implementations of the present disclosure. Further description of those implementations, and other implementations, are described in more detail below.

Other implementations may include a transitory or non-transitory computer readable medium storing instructions executable by one or more processors (e.g., central processing unit(s) (CPU(s)), graphics processing unit(s) (GPU(s)), and/or tensor processing unit(s) (TPU(s)) (such as included within a computing device) to perform a method such as one or more of the methods described above and/or elsewhere herein. Yet other implementations may include a system of one or more computers or computing devices and/or one or more databases that include one or more processors operable to execute stored instructions to perform a method such as one or more of the methods described above and/or elsewhere herein.

It should be appreciated that all combinations of the foregoing concepts and additional concepts described in greater detail herein are contemplated as being part of the subject matter disclosed herein. For example, all combinations of claimed subject matter appearing at the end of this disclosure are contemplated as being part of the subject matter disclosed herein. Thus, the features, functions, and advantages that have been discussed can be achieved independently in various examples or may be combined in yet other examples. Further details of the examples can be seen with reference to the following description and drawings.

BRIEF DESCRIPTION OF THE FIGURES

The novel features believed characteristic of the illustrative examples are set forth in the appended claims. The illustrative examples, however, as well as a preferred mode of use, further objectives and descriptions thereof, will best be understood by reference to the following detailed description of an illustrative example of the present disclosure when read in conjunction with the accompanying drawings, wherein:

DETAILED DESCRIPTION

Disclosed examples will now be described more fully hereinafter with reference to the accompanying drawings, in which some, but not all of the disclosed examples are shown. Indeed, several different examples may be described and should not be construed as limited to the examples set forth herein. Rather, these examples are described so that this disclosure will be thorough and complete and will fully convey the scope of the disclosure to those skilled in the art.

Within examples, receiving, real time, event-triggered diagnostic test results for an animal patient are utilized to create a pet owner profile for an owner of the animal patient, and the pet owner profile is used to match against data, within a product database, to identify a stored message and stored information relating to a product associated with recommended treatment for the animal patient. Following, an electronic message is generated and sent to a second computing device associated with the owner of the animal patient that includes the stored message and the stored information relating to the product associated with recommended treatment for the animal patient. Reports can be received indicating whether the owner of the animal patient obtained the product associated with recommended treatment for the animal patient, and further how many shipments of the product were received.

The systems and methods described herein provide a solution to enable veterinary clinics to increase at home treatment and care, as well as to improve data collection and accuracy for animal patient records. Implementations of this disclosure provide technological improvements that are particular to computer technology, for example, those concerning analysis and accuracy of animal patient records for further diagnostic evaluation and treatment. For example, implementation of this disclosure allows for correct updating of animal patient records to indicate treatment recommended, products obtained for treatment, and results of the treatment applied.

By mapping the existing logic inside patient information management systems (PIMS) and creating algorithms that connect the clinical interaction with the underlying data stores and programs associated with diagnosed conditions, computing devices can be algorithmically programmed to provide messages and information to pet owners to ensure that pet owners receive timely messages with protocols for successful at-home care and products that have proven clinically effective.

Figure 1:
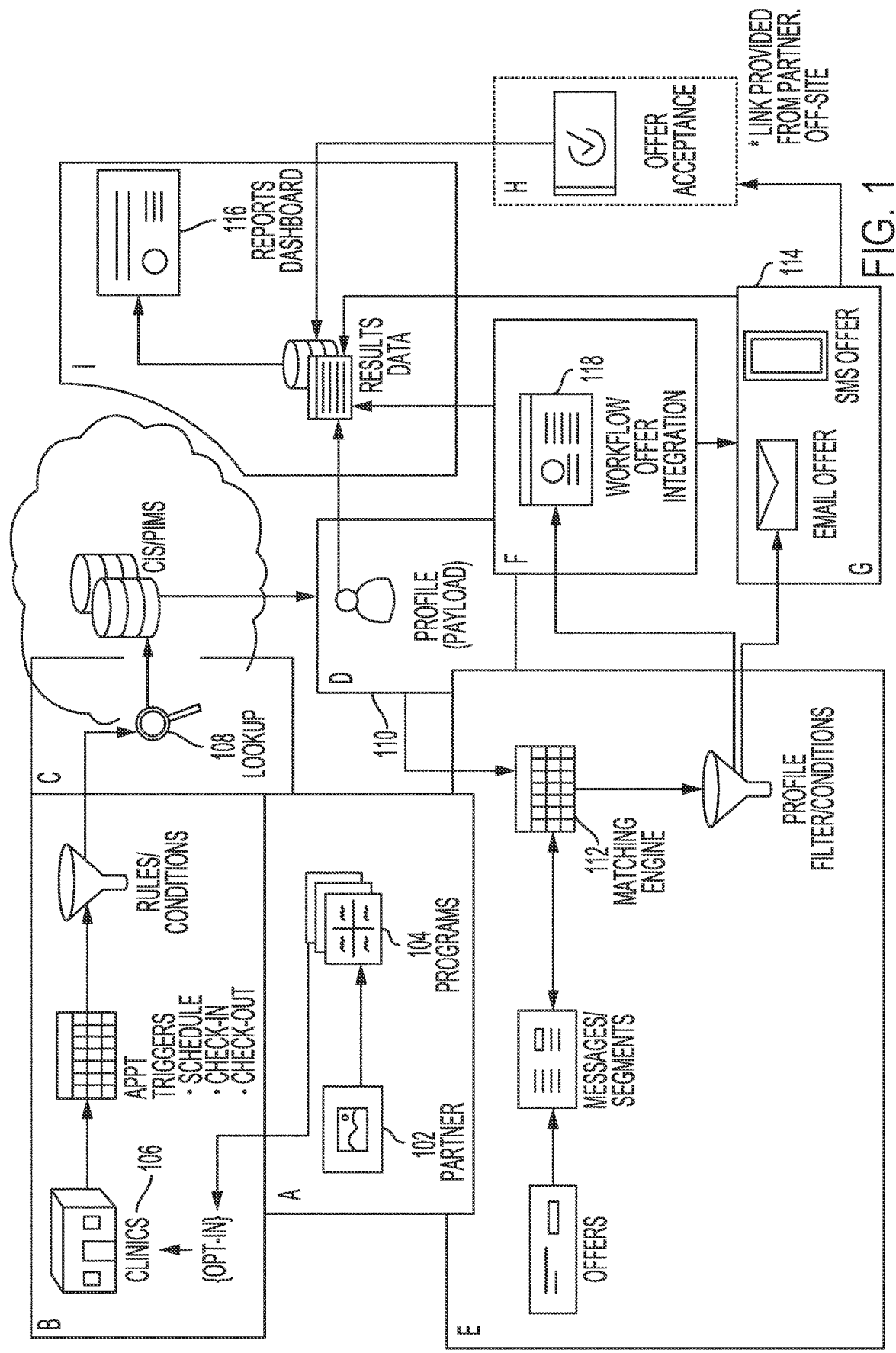
FIG. 1 illustrates an example workflow process for increasing veterinary health care compliance, according to an example implementation.

Referring now to the figures, FIG. 1 illustrates an example workflow process for increasing veterinary health care compliance, according to an example implementation. For veterinary practices or clinics, compliance protocols are created to increase pet owner awareness and fulfillment of recommended treatment for their animal patient. This can increase profits for partners, improve adherence to successful wellness protocols to benefit health of the animal patient, and transform clinic service via an algorithmically optimized customer experience.

An example compliance protocols platform creates real time, event-triggered prompts for owners of pets to prescribe the owners of recommended treatment and products to assist with the recommend treatment, as a result of a check-up at the veterinary practice. In FIG. 1, a veterinary clinic or third party partners 102 can develop programs 104 for use by veterinary clinics 106. The programs 104 can be associated with medical products for use with diagnosed conditions, as well as clinic endorsed treatment plans for the diagnosed conditions.

The programs 104 are designed to electronically enable protocols that work based on clinical experience by identifying indicators that yield a diagnosed condition, and using the indicators to trigger messaging to pet parents.

The veterinary clinics 106 can opt-in to enable the programs 104 they believe will be beneficial to their clients and to be a provider of the programs 104, for example.

The veterinary clinics 106 are establishments where owners of animals bring their animals for check-ups. The veterinary clinics 106 have access to patient information management systems (PIMS) (e.g., either directly or through a network or the cloud), in which information of the animal patient can be accessed and input. An event during the appointment of the animal patient can be used in real time as a trigger, based on programmed rules and conditions, for prescribed at-home care protocols to be generated and sent to the pet owner. Aspects of the appointment that can be used for this event trigger include scheduling of the appointment, a check-in during the appointment, or a check-out following completion of the appointment, for example. Any of these aspects can trigger clinic recommendations based on information changes in the PIMS, for example.

Once the event trigger occurs, a look-up application 108, residing on a server or computing device in communication with the PIMS, identifies patients eligible for prescribed protocols. Eligible owners of the animals are identified using data in a veterinary PIMS to create a pet owner profile 110. The pet owner profile can include information indicative of the pet, the pet owner, the event and the veterinary clinic.

The pet owner profile 110 is utilized by a matching engine 112 to identify messages and offers to incorporate into a message, such as an email message or short-message-service (SMS), or PIMS workflow integration 114, to be sent to the owner of the animal patient. The event trigger further indicates an appropriate time to send or display the message.

The matching engine 112 also identifies the clinic's e-pharmacy partner and integrates all information necessary between parties to ensure the pet parent can obtain any products in the recommended protocol with ease.

Following sending of the message, if the offer is accepted, a program partner will track and report on program conversions and report information back to a database for inclusion in a reports dashboard 116.

In some example, a program includes a workflow offer integration 118, an automated message will interrupt the process of the individual at the front desk, prompting a personalized offer to the pet parent that can be converted immediately using an existing process in the clinic. For example, prompts can be provided for clinic staff, based on live data from the PIMS, to create personalized suggestions based on successful protocols triggered by PIMS events. If the pet parent prefers to review the protocol at home and determine whether to accept the offer, the same type of algorithm can be applied to send protocol-based messaging in real time at check out. Eligible pet owners are identified using live data in veterinary patient information systems (including the results of diagnostic tests) to create the pet parent profile, and an event trigger that indicates the appropriate time to send or display a message. An algorithmically derived, personalized message is generated for a clinic staff member about the animal patient they are working with based on protocols that have achieved clinical and commercial success.

As one specific example, for animal patients who had a dental prophylaxis, the rules and conditions can indicate to generate and send a real time protocol prescription at check out, including a promotion/link to auto-ship a certain product (e.g., dental chews) from the clinic's e-pharmacy partner. The message can offer treatment recommendations, such as to integrate oral health into the animal patient's daily life (e.g., brush dog's teeth, or offer daily dental treats). The message can further offer advice on post-treatment side effects, such as a lower appetite for the animal or a mild cough after a procedure. The message further can recommend to track progress by following-up in two weeks, for example. The message also includes an offer or recommendation for a product associated with the recommended treatment, such as dental chews, and a hyperlink to a vendor to obtain the product, for example.

As another example, for animal patients who had a test for diseases associated or spread by parasites, an electronic protocol prescription can be generated and sent to the pet owner in real time, at check-out, including promotion/link to auto-ship a certain product (e.g., chewable medicine) from the clinic's e-pharmacy partner. The message can further offer a summary of results of the visit indicating whether heartworm disease, Lyme, Anaplasmosis, or Ehrlichiosis were found, and steps to protect and prevent contraction of these diseases.

As yet another example, for animal patients who were identified as obese on a Body Condition Scale (BCS) scale (4-5 on 5 pt, 7-8 on 9 pt scale), an electronic protocol prescription can be generated and sent in real time, at check out, including a promotion/link to auto-ship a certain product (e.g., dietary or weight management food) from the clinic's e-pharmacy partner. The message can indicate a current weight, previous weight, weight change, and information on recommend foods to offer to achieve a desired or ideal weight.

As used herein, "real time" refers to a time frame occurring at the trigger event. Thus, in real time at check out, refers to sending the message once check out has been completed or triggered. Real time can be considered "substantially" real time, and encompasses tolerances within a time frame of check out occurring, such as within 5-20 minutes.

Using the workflow shown in FIG. 1 enables the veterinary practice to reach the pet owner 1-2 days in advance of an appointment, as well as within 5-20 minutes after the appointment or in real time to offer recommendations for treatment. It has been found that such timeframes and follow-up periods have the best results for compliance as the pet owner is attentive to the recommendations and can receive better information to continue care at home.

Implementations of the workflow can be controlled or executed by a server or computing device in communication with the veterinary clinic 106 and PIMS, for example.

Figure 2:
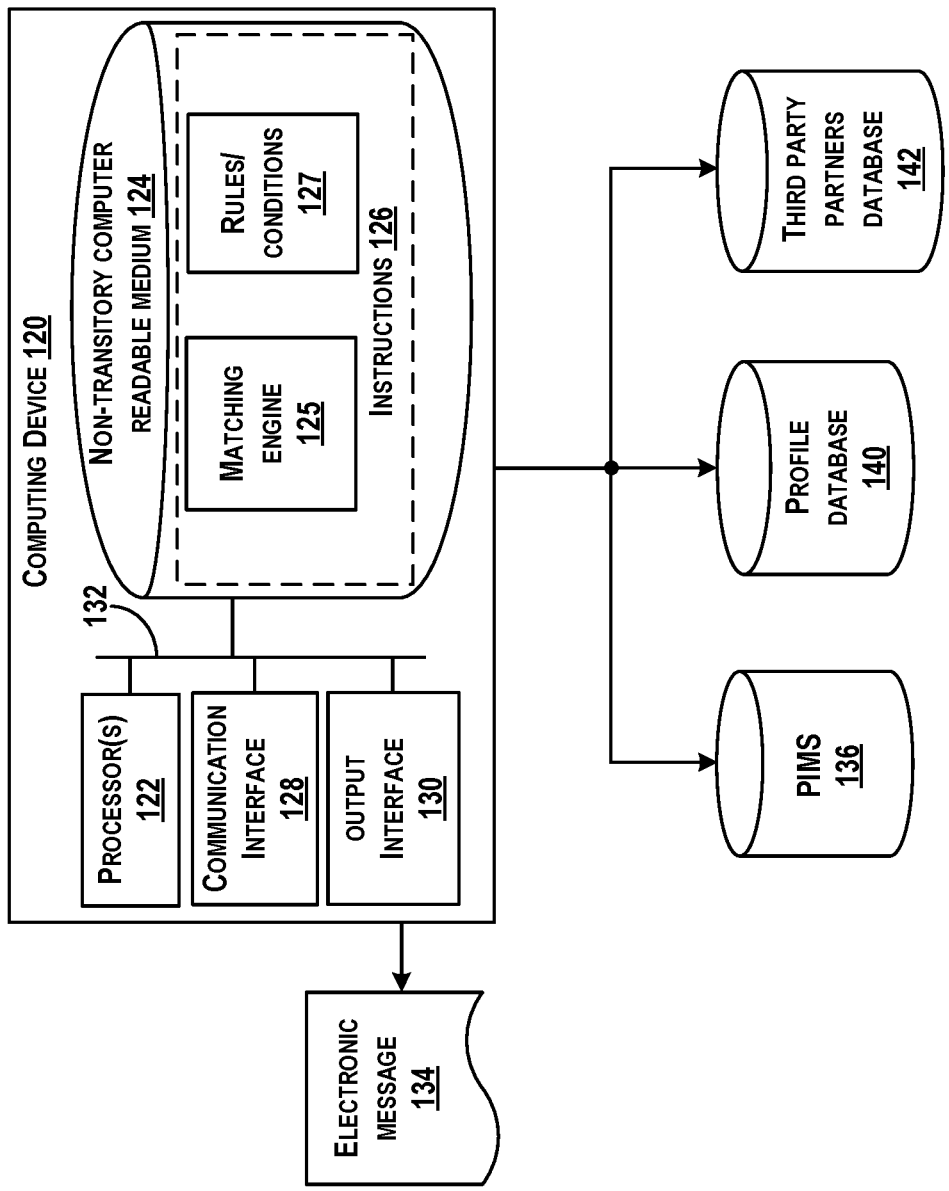
FIG. 2 illustrates an example of a computing device, according to an example implementation.

FIG. 2 illustrates an example of a computing device 120, according to an example implementation. The computing device 120 is coupled to or may be in communication with databases and clinics as shown in FIG. 1.

Within examples, the computing device 120 has one or more processor(s) 122 and non-transitory computer readable medium 124 storing instructions 126 executable by the one or more processors 122 to perform functions for generating and sending messages, as described herein. The instructions can further include a matching engine algorithm 125 and a rules/conditions algorithm 127. The computing device 120 is shown as a stand-alone component in FIG. 2. In some other examples, the computing device 120 may be incorporated within some of the components shown in FIG. 1.

To perform functions noted above, the computing device 120 also includes a communication interface 128, an output interface 130, and each component of the computing device 120 is connected to a communication bus 132. The computing device 120 may also include hardware to enable communication within the computing device 120 and between the computing device 120 and other devices (not shown). The hardware may include transmitters, receivers, and antennas, for example.

The communication interface 128 may be a wireless interface and/or one or more wireline interfaces that allow for both short-range communication and long-range communication to one or more networks or to one or more remote devices. Such wireless interfaces may provide for communication under one or more wireless communication protocols, Bluetooth, WiFi (e.g., an institute of electrical and electronic engineers (IEEE) 802.11 protocol), Long-Term Evolution (LTE), cellular communications, near-field communication (NFC), and/or other wireless communication protocols. Such wireline interfaces may include an Ethernet interface, a Universal Serial Bus (USB) interface, or similar interface to communicate via a wire, a twisted pair of wires, a coaxial cable, an optical link, a fiber-optic link, or other physical connection to a wireline network. Thus, the communication interface 128 may be configured to receive input data from one or more devices, and may also be configured to send output data to other devices.

The non-transitory computer readable medium 124 may include or take the form of memory, such as one or more computer-readable storage media that can be read or accessed by the one or more processor(s) 122. The non-transitory computer readable medium 124 can include volatile and/or non-volatile storage components, such as optical, magnetic, organic or other memory or disc storage, which can be integrated in whole or in part with the one or more processor(s) 122. In some examples, the non-transitory computer readable medium 124 can be implemented using a single physical device (e.g., one optical, magnetic, organic or other memory or disc storage unit), while in other examples, the non-transitory computer readable medium 124 can be implemented using two or more physical devices. The non-transitory computer readable medium 124 thus is a computer readable storage, and the instructions 126 are stored thereon. The instructions 126 include computer executable code.

The one or more processor(s) 122 may be general-purpose processors or special purpose processors (e.g., digital signal processors, application specific integrated circuits, etc.). The one or more processor(s) 122 may receive inputs from the communication interface 128 (e.g., x-ray images), and process the inputs to generate outputs that are stored in the non-transitory computer readable medium 124. The one or more processor(s) 122 can be configured to execute the instructions 126 (e.g., computer-readable program instructions) that are stored in the non-transitory computer readable medium 124 and are executable to provide the functionality of the computing device 120 described herein.

The output interface 130 outputs information for reporting or storage (e.g., an electronic message, or a report 134), and thus, the output interface 130 may be similar to the communication interface 128 and can be a wireless interface (e.g., transmitter) or a wired interface as well.

The computing device 120 can also include or be coupled to a number of databases, such as a PIMS 136, a profile database 140, and a third party partners database 142. In FIG. 2, the additional databases are shown as separate components of the computing device 120; however, each database may alternatively be integrated within the computing device 120. Access of the databases further enables the computing device 120 to perform functions as described herein. Functionality and content of the databases is described below.

The PIMS 136 (Patient Information Management System) is the veterinary clinic's database of record. The PIMS 136 contains information about all products, services, clients (demographic information), patients, prescription recommendations, medical notes, invoices, and other data related to a visit to a veterinary clinic, and over the lifetime involvement with a client.

The profile datastore 140 is a data store that holds and stores relevant programmatic information for eligible pet parents from a clinic.

The third party partners database 142 is a database that holds product, clinic, patient, and client data for ecommerce, pharma or nutrition partners.

Within one example, in operation, when the instructions 112 are executed by the one or more processor(s) 108, the one or more processor(s) 108 are caused to perform functions as shown and described below with reference to the flowchart in FIG. 3.

Figure 3:
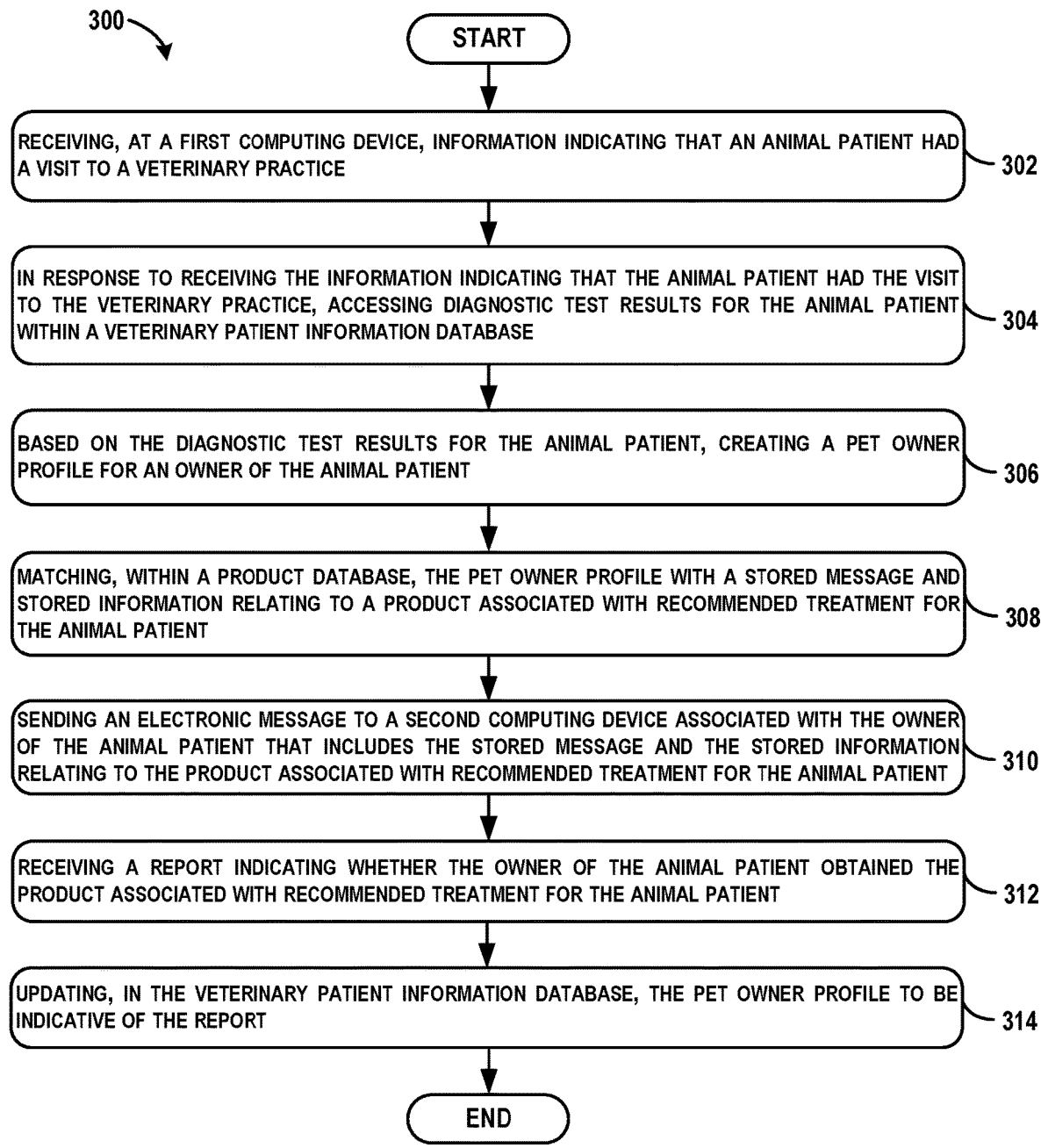
FIG. 3 shows a flowchart of another example of a computer-implemented method for increasing veterinary health care compliance, according to an example implementation.

FIG. 3 shows a flowchart of another example of a computer-implemented method 300 for increasing veterinary health care compliance, according to an example implementation. Method 300 shown in FIG. 3 presents an example of a method that could be used with the computing device 120 shown in FIG. 2, for example. Further, devices or systems may be used or configured to perform logical functions presented in FIG. 3. In some instances, components of the devices and/or systems may be configured to perform the functions such that the components are actually configured and structured (with hardware and/or software) to enable such performance. In other examples, components of the devices and/or systems may be arranged to be adapted to, capable of, or suited for performing the functions, such as when operated in a specific manner. Method 300 may include one or more operations, functions, or actions as illustrated by one or more of blocks 302-314. Although the blocks are illustrated in a sequential order, these blocks may also be performed in parallel, and/or in a different order than those described herein. Also, the various blocks may be combined into fewer blocks, divided into additional blocks, and/or removed based upon the desired implementation.

It should be understood that for this and other processes and methods disclosed herein, flowcharts show functionality and operation of one possible implementation of present examples. In this regard, each block or portions of each block may represent a module, a segment, or a portion of program code, which includes one or more instructions executable by a processor for implementing specific logical functions or steps in the process. The program code may be stored on any type of computer readable medium or data storage, for example, such as a storage device including a disk or hard drive. Further, the program code can be encoded on a computer-readable storage media in a machine-readable format, or on other non-transitory media or articles of manufacture. The computer readable medium may include non-transitory computer readable medium or memory, for example, such as computer-readable media that stores data for short periods of time like register memory, processor cache and Random Access Memory (RAM). The computer readable medium may also include non-transitory media, such as secondary or persistent long term storage, like read only memory (ROM), optical or magnetic disks, compact-disc read only memory (CD-ROM), for example. The computer readable media may also be any other volatile or non-volatile storage systems. The computer readable medium may be considered a tangible computer readable storage medium, for example.

In addition, each block or portions of each block in FIG. 3, and within other processes and methods disclosed herein, may represent circuitry that is wired to perform the specific logical functions in the process. Alternative implementations are included within the scope of the examples of the present disclosure in which functions may be executed out of order from that shown or discussed, including substantially concurrent or in reverse order, depending on the functionality involved, as would be understood by those reasonably skilled in the art.

At block 302, the method 300 includes receiving, at a first computing device, information indicating that an animal patient concluded a visit at a veterinary practice. This can include the first computing device accessing the veterinary clinic or being sent a message indicating that the animal patient has check-out following a visit. In one example, existing logic inside the PIMS 136 is mapped to connect the clinical interaction with the underlying data stores and programs associated with diagnosed conditions. Underlying data stores are monitored as a trigger to disperse prescribed protocols to eligible pet parents.

At block 304 the method 300 includes in response to receiving the information indicating that the animal patient concluded the visit at the veterinary practice, accessing diagnostic test results for the animal patient within a veterinary patient information database.

At block 306, the method 300 includes based on the diagnostic test results for the animal patient, creating a pet owner profile for an owner of the animal patient. Profiles include clinic messaging opt-in status, channel preference, number and frequency of messages received by clinic and diagnostic results information, along with other programmatic information, for example.

At block 308, the method 300 includes matching, within a product database, the pet owner profile with a stored message and stored information relating to a product associated with recommended treatment for the animal patient. Products from the clinic's e-pharmacy partner are eligible for inclusion in a protocol, and clinics can select products upon enrollment.

At block 310, the method 300 includes sending an electronic message to a second computing device associated with the owner of the animal patient that includes the stored message and the stored information relating to the product associated with recommended treatment for the animal patient.

Within examples sending the electronic message include sending the electronic message including the stored information and a hyperlink to a vender to obtain the product. The message can be sent within about 5 minutes to about 10 minutes of receipt of the information indicating that the animal patient concluded the visit at the veterinary practice.

At block 312, the method 300 includes receiving a report indicating whether the owner of the animal patient was sent a prescribed protocol, whether the owner of the animal patient opened a message, whether the owner of the animal patient visited the clinic's e-pharmacy, whether the owner of the animal patient obtained the product associated with recommended treatment for the animal patient, and whether the owner of the animal patient received successive delivery via an auto-ship subscription.

At block 314, the method 300 includes updating, in the veterinary patient information database, the pet owner profile to be indicative of the report.

In some examples, the method 300 can also include based on the diagnostic test results, sending the report indicating that the owner of the animal patient has not obtained the product associated with recommended treatment for the animal patient, sending a follow-up electronic message to the second computing device.

In some examples, the method 300 can include generating an interrupt message prompting a personalized offer for the owner of the animal patient, and sending the interrupt message to a third computing device at the veterinary practice to ensure that clinical staff educates the owner of the animal patient on the prescribed protocol and personalized offer.

In a specific example, the diagnostic test results for the animal patient include a Body Condition Scale (BCS) result, a weight of the animal patient, and a previous weight of the animal patient during a previous visit at the veterinary practice. The method 300 can then additionally include based on the BCS result, the weight of the animal patient, and a change in weight of the animal patient as compared to the previous visit at the veterinary practice, updating the pet owner profile, and matching, within the product database, the pet owner profile includes matching the updated pet owner profile.

Additional or alternative methods of increasing veterinary health care compliance can be provided or executed by the computing device 120. An example additional method includes providing a patient information management system (PIMS), providing a database having veterinary medical information including, dental, weight and parasite presence/absence information, pet owner information including, email and phone information, and a software algorithm executable to identify medical information eligible for messaging based on predetermined protocols. Following, this additional method includes generating a message to the pet owner via email and/or phone within 24 hours of new medical information relating to dental, weight or parasite presence/absence being added to the database, and the message can include the availability of veterinary products at discounted rates and internet links to order such products. The additional method thus includes executing the software algorithm, via a processor, to identify the medical information eligible for messaging based on diagnostic test results of an animal patient being below a threshold and a report indicating that an owner of the animal patient has not obtained a product associated with recommended treatment for the animal patient. Following, further optional functions include sending a follow-up electronic message to the pet owner with information to remind the pet owner of the recommended treatment.

Utilizing methods described herein enables verification of at home treatment, in certain instances, which can be useful to verify if treatment is effective at a subsequent visit. If some products are not as effective, new recommendations can be generated. A library of protocols and offers can be generated over time based on the updated results seen at each veterinary clinic.

Example methods and systems described herein thus utilize rules and conditions to identify appropriate recommendations and products for treatment per individual animal patient.

By the term "substantially" and "about" used herein, it is meant that the recited characteristic, parameter, or value need not be achieved exactly, but that deviations or variations, including for example, tolerances, measurement error, measurement accuracy limitations and other factors known to skill in the art, may occur in amounts that do not preclude the effect the characteristic was intended to provide.

Different examples of the system(s), device(s), and method(s) disclosed herein include a variety of components, features, and functionalities. It should be understood that the various examples of the system(s), device(s), and method(s) disclosed herein may include any of the components, features, and functionalities of any of the other examples of the system(s), device(s), and method(s) disclosed herein in any combination or any sub-combination, and all of such possibilities are intended to be within the scope of the disclosure.

The description of the different advantageous arrangements has been presented for purposes of illustration and description, and is not intended to be exhaustive or limited to the examples in the form disclosed. Many modifications and variations will be apparent to those of ordinary skill in the art. Further, different advantageous examples may describe different advantages as compared to other advantageous examples. The example or examples selected are chosen and described in order to best explain the principles of the examples, the practical application, and to enable others of ordinary skill in the art to understand the disclosure for various examples with various modifications as are suited to the particular use contemplated.

What is claimed is:

1. A computer-implemented method of increasing veterinary health care compliance, comprising:
   receiving, at a first computing device, information indicating that an animal patient had a visit to a veterinary practice;
   in response to receiving the information indicating that the animal patient had the visit to the veterinary practice, accessing diagnostic test results for the animal patient within a veterinary patient information database;
   based on the diagnostic test results for the animal patient, (i) identifying the animal patient as eligible for prescribed protocols that link products available for delivery associated with recommended treatment for the animal patient, and then (ii) creating a pet owner profile for an owner of the animal patient;
   matching, within a product database, the pet owner profile with a stored message and stored information relating to a product associated with the recommended treatment for the animal patient;
   sending an electronic message to a second computing device associated with the owner of the animal patient that includes the stored message, the stored information relating to the product associated with the recommended treatment for the animal patient, and a hyperlink to a vendor to obtain the product;
   generating a report, via an e-pharmacy being accessed via the hyperlink, indicating whether the owner of the animal patient obtained the product associated with recommended treatment for the animal patient; and
   updating, in the veterinary patient information database, the pet owner profile to be indicative of the report.

2. The method of claim 1, wherein sending the electronic message comprises:
   sending the electronic message within about 5 minutes to about 10 minutes of receipt of the information indicating that the animal patient concluded the visit at the veterinary practice.

3. The method of claim 1, further comprising:
   based on the diagnostic test results being below a threshold and the report indicating that the owner of the animal patient has not obtained the product associated with recommended treatment for the animal patient, sending a follow-up electronic message to the second computing device.

4. The method of claim 1, further comprising:
   generating an interrupt message prompting that a personalized offer be made to the owner of the animal patient by clinic staff; and
   sending the interrupt message to a third computing device at the veterinary practice to enable the clinic staff to accept the personalized offer on behalf of the owner of the animal patient.

5. The method of claim 1,
   wherein accessing the diagnostic test results for the animal patient comprises accessing a dental exam result;
   and the method further comprises:
   based on the dental exam result, updating the pet owner profile; and
   wherein matching, within the product database, the pet owner profile comprises matching the updated pet owner profile.

6. The method of claim 1,
   wherein accessing the diagnostic test results for the animal patient comprises accessing a Body Condition Scale (BCS) result, a weight of the animal patient, and a previous weight of the animal patient during a previous visit at the veterinary practice;
   and the method further comprises:
   based on the BCS result, the weight of the animal patient, and a change in weight of the animal patient as compared to the previous visit at the veterinary practice, updating the pet owner profile; and wherein matching, within the product database, the pet owner profile comprises matching the updated pet owner profile.

7. The method of claim 1, further comprising:

based on a check-out following completion of the visit to the veterinary practice within a patient information management system (PIM), sending the electronic message to the second computing device.

8. A system comprising:

one or more processors; and non-transitory computer readable medium storing instructions executable by the one or more processors to perform functions comprising:

receiving information indicating that an animal patient had a visit to a veterinary practice;

in response to receiving the information indicating that the animal patient had the visit to the veterinary practice, accessing diagnostic test results for the animal patient within a veterinary patient information database;

based on the diagnostic test results for the animal patient, (i) identifying the animal patient as eligible for prescribed protocols that link products available for delivery associated with recommended treatment for the animal patient, and then (ii) creating a pet owner profile for an owner of the animal patient;

matching, within a product database, the pet owner profile with a stored message and stored information relating to a product associated with the recommended treatment for the animal patient;

sending an electronic message to a second computing device associated with the owner of the animal patient that includes the stored message, the stored information relating to the product associated with the recommended treatment for the animal patient, and a hyperlink to a vendor to obtain the product;

generating a report, via an e-pharmacy being accessed via the hyperlink, indicating whether the owner of the animal patient obtained the product associated with recommended treatment for the animal patient; and updating, in the veterinary patient information database, the pet owner profile to be indicative of the report.

9. The system of claim 8, wherein sending the electronic message comprises:

sending the electronic message within about 5 minutes to about 10 minutes of receipt of the information indicating that the animal patient concluded the visit at the veterinary practice.

10. The system of claim 8, wherein the functions further comprise:

based on the diagnostic test results being below a threshold and the report indicating that the owner of the animal patient has not obtained the product associated with recommended treatment for the animal patient, sending a follow-up electronic message to the second computing device.

11. The system of claim 8, wherein the functions further comprise:

generating an interrupt message prompting that a personalized offer be made to the owner of the animal patient by clinic staff; and sending the interrupt message to a third computing device at the veterinary practice to enable the clinic staff to accept the personalized offer on behalf of the owner of the animal patient.

12. A non-transitory computer readable medium having stored thereon instructions, that when executed by one or more processors of a computing device, cause the computing device to perform functions comprising:

receiving, at the computing device, information indicating that an animal patient had a visit to a veterinary practice;

in response to receiving the information indicating that the animal patient had the visit to the veterinary practice, accessing diagnostic test results for the animal patient within a veterinary patient information database;

based on the diagnostic test results for the animal patient, (i) identifying the animal patient as eligible for prescribed protocols that link products available for delivery associated with recommended treatment for the animal patient, and then (ii) creating a pet owner profile for an owner of the animal patient;

matching, within a product database, the pet owner profile with a stored message and stored information relating to a product associated with the recommended treatment for the animal patient;

sending an electronic message to a second computing device associated with the owner of the animal patient that includes the stored message, the stored information relating to the product associated with the recommended treatment for the animal patient, and a hyperlink to a vendor to obtain the product;

generating a report, via an e-pharmacy being accessed via the hyperlink, indicating whether the owner of the animal patient obtained the product associated with recommended treatment for the animal patient; and updating, in the veterinary patient information database, the pet owner profile to be indicative of the report.

13. The non-transitory computer readable medium of claim 12, wherein sending the electronic message comprises:

sending the electronic message within about 5 minutes to about 10 minutes of receipt of the information indicating that the animal patient concluded the visit at the veterinary practice.

14. The non-transitory computer readable medium of claim 12, wherein the functions further comprise:

based on the diagnostic test results being below a threshold and the report indicating that the owner of the animal patient has not obtained the product associated with recommended treatment for the animal patient, sending a follow-up electronic message to the second computing device.

15. The non-transitory computer readable medium of claim 12, wherein the functions further comprise:

generating an interrupt message prompting that a personalized offer be made to the owner of the animal patient by clinic staff; and sending the interrupt message to a third computing device at the veterinary practice to enable the clinic staff to accept the personalized offer on behalf of the owner of the animal patient.

* * * * *